United States Patent
Sanchez

(10) Patent No.: US 9,456,880 B1
(45) Date of Patent: Oct. 4, 2016

(54) DENTAL WEDGE WITH A FLEXIBLE TUBING SUCTION LINE

(76) Inventor: George A Sanchez, Port Charlotte, FL (US)

( * ) Notice: Subject to any disclaimer, the term of this patent is extended or adjusted under 35 U.S.C. 154(b) by 0 days.

(21) Appl. No.: 13/317,324

(22) Filed: Oct. 14, 2011

(51) Int. Cl.
  *A61C 17/06* (2006.01)
  *A61C 17/14* (2006.01)
  *A61C 5/12* (2006.01)

(52) U.S. Cl.
  CPC ............ *A61C 5/127* (2013.01); *A61C 17/043* (2013.01)

(58) Field of Classification Search
  CPC ..... A61C 17/043; A61C 17/04; A61C 5/127
  USPC ...... 433/39, 91–96, 136, 148–149; 600/156; 604/35, 118–121, 131, 151–155, 264, 604/268, 902; 15/415.1, 419, 421
  See application file for complete search history.

(56) References Cited

U.S. PATENT DOCUMENTS

| | | | |
|---|---|---|---|
| 3,636,631 A * | 1/1972 | Tofflemire | 433/149 |
| 3,890,714 A | 6/1975 | Gores | |
| 4,068,664 A * | 1/1978 | Sharp et al. | 604/268 |
| 4,265,621 A * | 5/1981 | McVey | 433/91 |
| 4,468,199 A | 8/1984 | Weikel | |
| 4,802,851 A * | 2/1989 | Rhoades | 433/93 |
| 5,078,603 A * | 1/1992 | Cohen | 433/91 |
| 5,145,368 A * | 9/1992 | Tomic | 433/91 |
| 5,573,400 A | 11/1996 | Asher | |
| 5,688,121 A * | 11/1997 | Davis | 433/96 |
| 5,813,856 A * | 9/1998 | Lee | 433/31 |
| 5,924,866 A * | 7/1999 | Eldreth | 433/140 |
| 6,007,334 A * | 12/1999 | Suhonen | 433/39 |
| 6,024,566 A * | 2/2000 | Bruns et al. | 433/136 |
| 6,309,218 B1 * | 10/2001 | Ellenbecker | 433/93 |
| 6,482,007 B2 * | 11/2002 | Stanwich et al. | 433/149 |
| 6,736,640 B1 * | 5/2004 | Ellenbecker | 433/93 |

(Continued)

OTHER PUBLICATIONS

Madhusudhana Koppolu, Dorasani GoGalm, Effect of Saliva and Blood Contamination of the Bowd Strength of Self-Etching Adhesive System. Journal of Conservative Dentistry 2012, vol. 15 Issue: 3 p. 270-273.

(Continued)

*Primary Examiner* — Matthew Nelson
(74) *Attorney, Agent, or Firm* — Bishop Diehl & Lee, Ltd.

(57) ABSTRACT

A dental wedge device, comprising of a hollow body with perforations on all three sides of a general triangular cross section, is coupled to a flexible tubing which can be connected to a dental vacuum device, readily available in a dental operatory. The dental wedge device incorporates a novel element that addresses a major issue of moisture control. Moisture contamination of a dental restoration during placement will compromise the longevity of the restorative material. The perforated sides of the wedge allow any moisture including gingival fluids, saliva and blood to be aspirated from the cavity preparation into a suction chamber. The fluids are then drawn into the flexible tubing line for complete ejection into a dental vacuum device. Another embodiment is described and shown.

6 Claims, 4 Drawing Sheets

(56) References Cited

U.S. PATENT DOCUMENTS

| | | | |
|---|---|---|---|
| 7,066,917 B2* | 6/2006 | Talamonti | 604/320 |
| 7,425,130 B2 | 9/2008 | Schaffner | |
| 2005/0239014 A1* | 10/2005 | Frider et al. | 433/31 |
| 2006/0252006 A1* | 11/2006 | Apelker et al. | 433/88 |
| 2007/0276326 A1* | 11/2007 | DiGasbarro | 604/131 |
| 2009/0311648 A1* | 12/2009 | Clasen et al. | 433/31 |
| 2010/0297575 A1* | 11/2010 | Effenberger et al. | 433/87 |

OTHER PUBLICATIONS

Chang SW, Cho BH, Lim RY, Kyung, Park DS, Oh TS, Effects of Blood Contamination on Microtensile Bond Strength to Dentin of Three Self-Etch Adhesive S, Oper Dent 2010; 35; 330-6.

Dietrich T, Kraemer ML, Roulet JF, Blood Contamination and Dplatin Bonding—Effect of Anticoagulant in Laboratory Studies. Dent Mater 2002; 18: 159-62.

* cited by examiner

DENTAL WEDGE WITH A FLEXIBLE TUBING SUCTION LINE

BACKGROUND

1.) Field of the Invention

The embodiment disclosed herein is in the field of dental instruments. More specifically, the embodiment relates to dental wedges that are used in dental procedures for restoring carious teeth.

2.) Prior Art

Restoration of cavities between teeth is a daily part of dentistry. When these carious lesions destroy the exterior tooth surface, a matrix band is placed around the prepared tooth to help retain the restorative material in place and thus provide for a proper anatomic shape of the repaired tooth.

The dental wedge has been used between teeth to help adapt the matrix band to the tooth being restored to keep moisture out and also to help separate teeth. FIG. 1 demonstrates a dental wedge of the prior art. Unfortunately, proper band adaptation can be difficult to achieve in part due to many variations in tooth contours. A loose fitting matrix band can allow blood, saliva or other contaminants to seep into the dry cavity preparation. Moisture contamination of the dental restoration will compromise the longevity of the restorative material.

Inventors have been filing patent applications to solve this problem.

U.S. Pat. No. 3,890,714 to Gores (1975) attempted to solve the problem by using a folded plastic wedge. This wedge can lacerate gingival tissue, creating more bleeding.

U.S. Pat. No. 4,468,199 to Weikel (1984) attempts to develop a less traumatic wedge by impregnating a hemostatic agent into the dental wedge to help control the bleeding, but does not address other forms of moisture such as saliva or crevicular fluid surrounding the matrix band.

U.S. Pat. No. 5,573,400 to Asher (1996) claims to solve this problem by using an expanding dental wedge, which absorbs moisture but does nothing to draw the moisture away from the cavity preparation. Any movement around the band may cause the saturated wedge to contaminate the cavity preparation.

Prior wedges have included various forms of wedge designs that try to address the problem of moisture contamination but make no attempt to aspirate the moisture away from the cavity preparation. What is needed is a wedge coupled to a dental vacuum device that aspirates the moisture away from the cavity preparation.

What is also needed is a dental wedge that can be easily removed from the oral cavity in the event a wedge inadvertently dislodges into the back of the throat. Aspiration of a dental wedge into the airway can lead to a serious medical emergency.

U.S. Pat. No. 6,482,007 to Stanwich, et at (2002) addresses this problem by attaching a removable handle to permit easy placement, but does not address the potential problem of removing the wedge when the handle is discarded. When the handle is removed, the operator needs to be careful to not lose the grip on the dental wedge.

U.S. Pat. No. 7,425,130 to Schaffner, et at (2008) tries to improve the safety by creating a pocket recess wherein a gripping instrument can engage it. This works well as long as the operator maintains a solid grip. Failure to maintain a solid grip may cause the operator to drop the wedge into the oral cavity.

SUMMARY OF THE INVENTION

1. The present invention is a dental wedge having flexible tubing attached thereto. Flexible tubing is attached to the dental wedge body so as to allow moisture to be aspirated away from the cavity preparation. The flexible tubing is connected into a vacuum line readily available in a dental operatory.

Accordingly, it is an object to easily retrieve the dental wedge when it dislodges into the oral cavity.

These features will become readily apparent in view of the following more detailed description.

DRAWINGS

Figures

The appended drawings depict only embodiments of the invention and are therefore not to be considered limiting of its scope.

DRAWINGS

Reference Numerals

Figure 1:
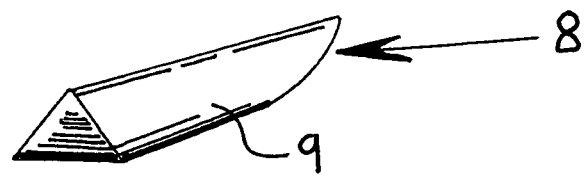
FIG. 1 is a view of a conventional dental wedge of the prior art.

5. A dental wedge of the present invention
6. Alternate embodiment
7. Sectional line
8. Conventional dental wedge of prior art
9. Body of dental wedge of prior art
10. Body of dental wedge of the present invention
11. Body of Alternate Embodiment
15. Perforations
20. Round distal end of flexible tubing
21. Round distal end of flexible tubing of alternate embodiment
25. Thin apex
30. Wide base
32. Suction chamber
35. Flexible tubing
37. Bendable portion of alternate embodiment
40. Distal insertion end of body
45. Proximal end of body
50. Proximal, open end of flexible tubing
51. Proximal end of flexible tubing of alternate embodiment
55. Cotton pliers
60. Matrix band
61. Gingiva
65. Molar with cavity preparation
66. Premolar
80. Specialized adapter device
81. Tubular sleeve
82. Apertures 83. Shaft
84. Top cap end
85. Direction of flow
86. Lower open end

DETAILED DESCRIPTION OF THE PREFERRED EMBODIMENTS

Figure 2:
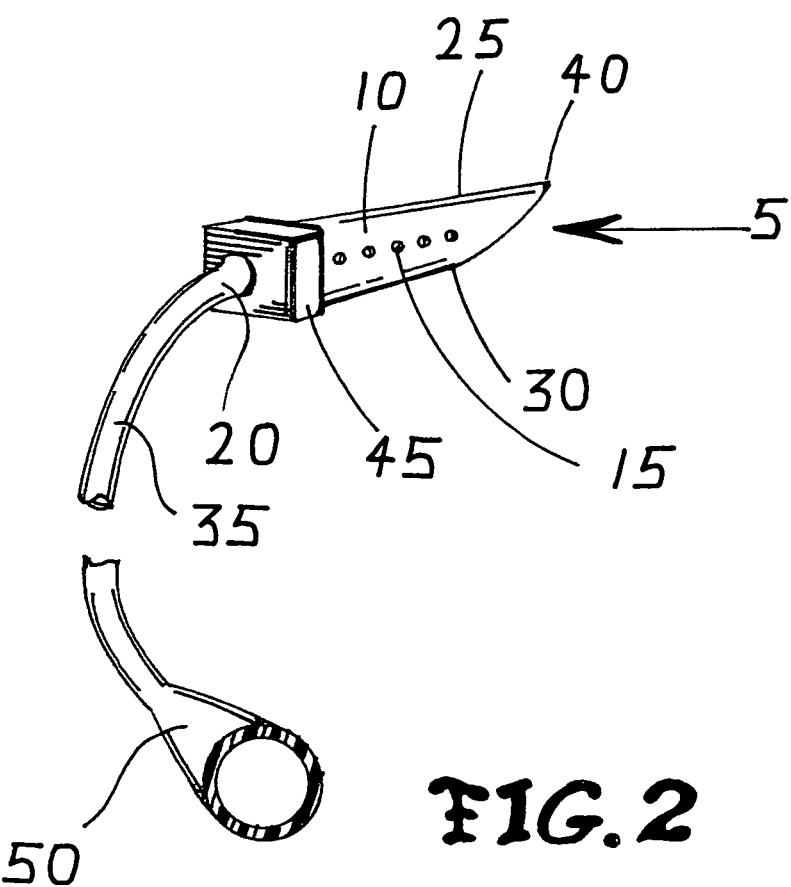
FIG. 2 is a perspective view of embodiment of a dental wedge of the present invention.
Figure 3:
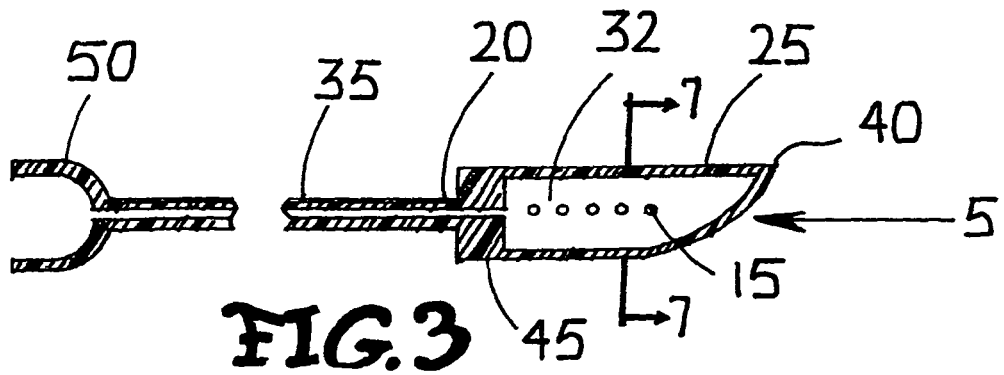
FIG. 3 is a cross-sectional view of the body and flexible tubing of the dental wedge shown in FIG. 2.
Figure 4:
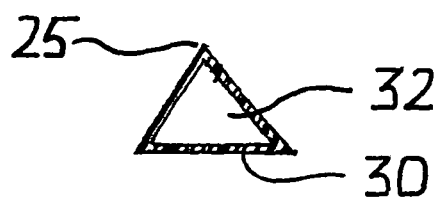
FIG. 4 is a sectional view taken through line 7-7 of FIG. 3.
Figure 5:
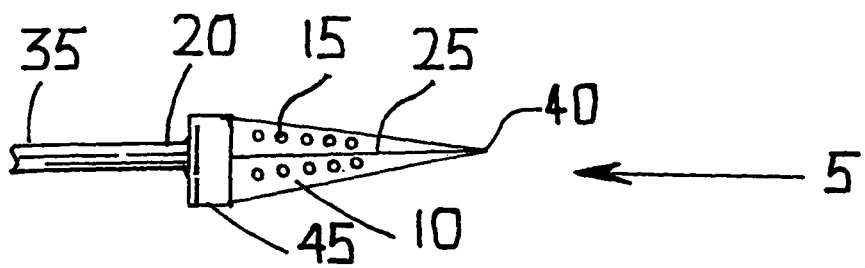
FIG. 5 is a top view of the body and of the flexible tubing of the dental wedge shown in FIG. 2.
Figure 6:
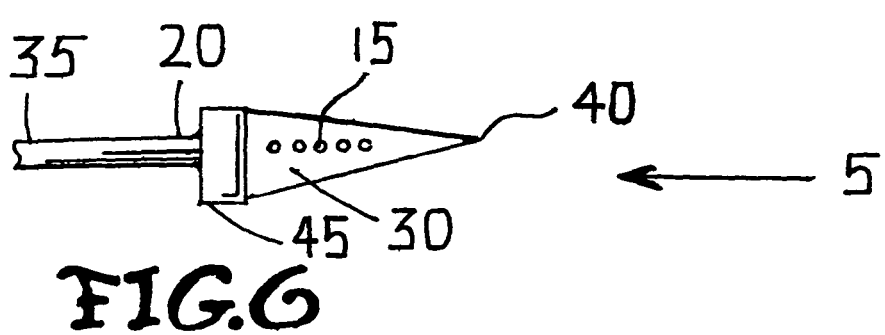
FIG. 6 is a bottom view of the body and of the flexible tubing of the dental wedge shown in FIG. 2.

As shown in FIG. 2, a dental wedge 5 of the present invention is comprised of a body 10 having a distal insertion end 40 and a square proximal end 45 coupled to round distal end of flexible tubing 20. The body 10 consists of a hollow rigid plastic material having a multiplicity of perforations 15 on all three sides of triangular walls as shown in FIGS. 5-6. FIG. 3 shows a cross sectional view of the body 10 and flexible tubing 35 of the embodiment. As shown in FIGS. 3-4, the body comprises of a hollow suction chamber 32 that leads directly into the tubing 20. However, the suction chamber 32 may be comprised of any suitable porous material that will allow moisture to pass through it. The hollow body 10 and tubing 35 consists of a plastic material but other materials may also be suitable.

The body of the wedge may have any configuration in different sizes suitable for insertion into a space between two teeth. As shown in FIG. 2, the preferred configuration of the body 10 of the wedge generally has a relatively thin distal insertion end with a wide base 30 that is relatively curved and which terminates at a pointed tip 40. FIG. 4 shows a sectional view taken through line 7-7 of FIG. 3 showing the wide base 30 and thin apex 25 of body 10. The body preferably flares from the distal insertion end toward the proximal end 45 such that the body has a triangular cross-section of increasing size, transitioning into a square flat surface formed perpendicular to the longitudinal axis, at the proximal end of the body 45. The tubing 35 continues to the proximal open end of flexible tubing 50 where it terminates. The proximal open end of tubing 50 flares to a larger diameter for insertion into a suitable dental vacuum device, not shown.

Figure 7:
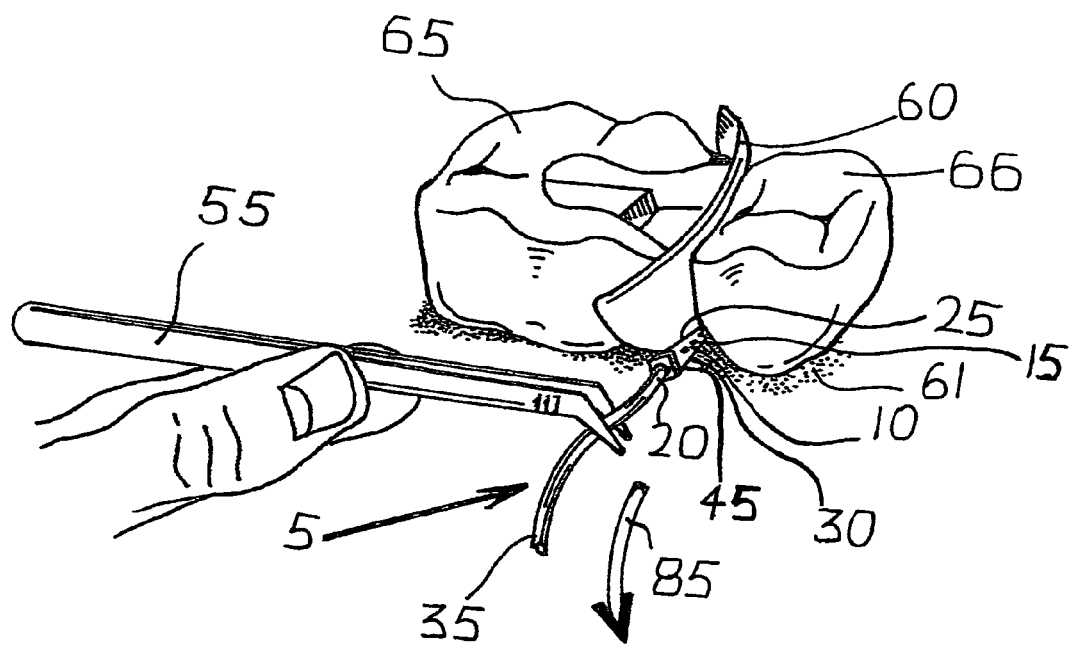
FIG. 7 is a perspective view of an operator's hand grasping the dental wedge with cotton pliers.

As shown in FIG. 7, an operator can easily grasp the dental wedge with conventional cotton pliers 55. The wide base 30 of the dental wedge 5 is located toward the gingiva 61 and the thin apex 25 extends between the molar 65 and the premolar 66 away from the gingiva 61. The dental wedge 5 can be inserted completely into position by grasping the distal end of tubing 20 with cotton pliers 55 and by pushing against the square face of the proximal end of the body 45. The round configuration of the distal end of tubing 20 permits the operator to grasp the dental wedge 5 from a variety of different gripping angles and positions, thereby, allowing the operator to comfortably insert the dental wedge 5 more easily. A traumatic insertion may lacerate the gingiva creating bleeding around the cavity preparation.

As shown in FIG. 7, when suction is applied to the body 10, the fluids in the adjacent gingival area will be drawn through the perforations 15 into the suction chamber 32. The fluids will then be drawn into the tubing 35 in the direction of arrow 85, which connects to a suitable dental vacuum device, not shown.

FIG. 8

Alternate Embodiment

Figure 8:
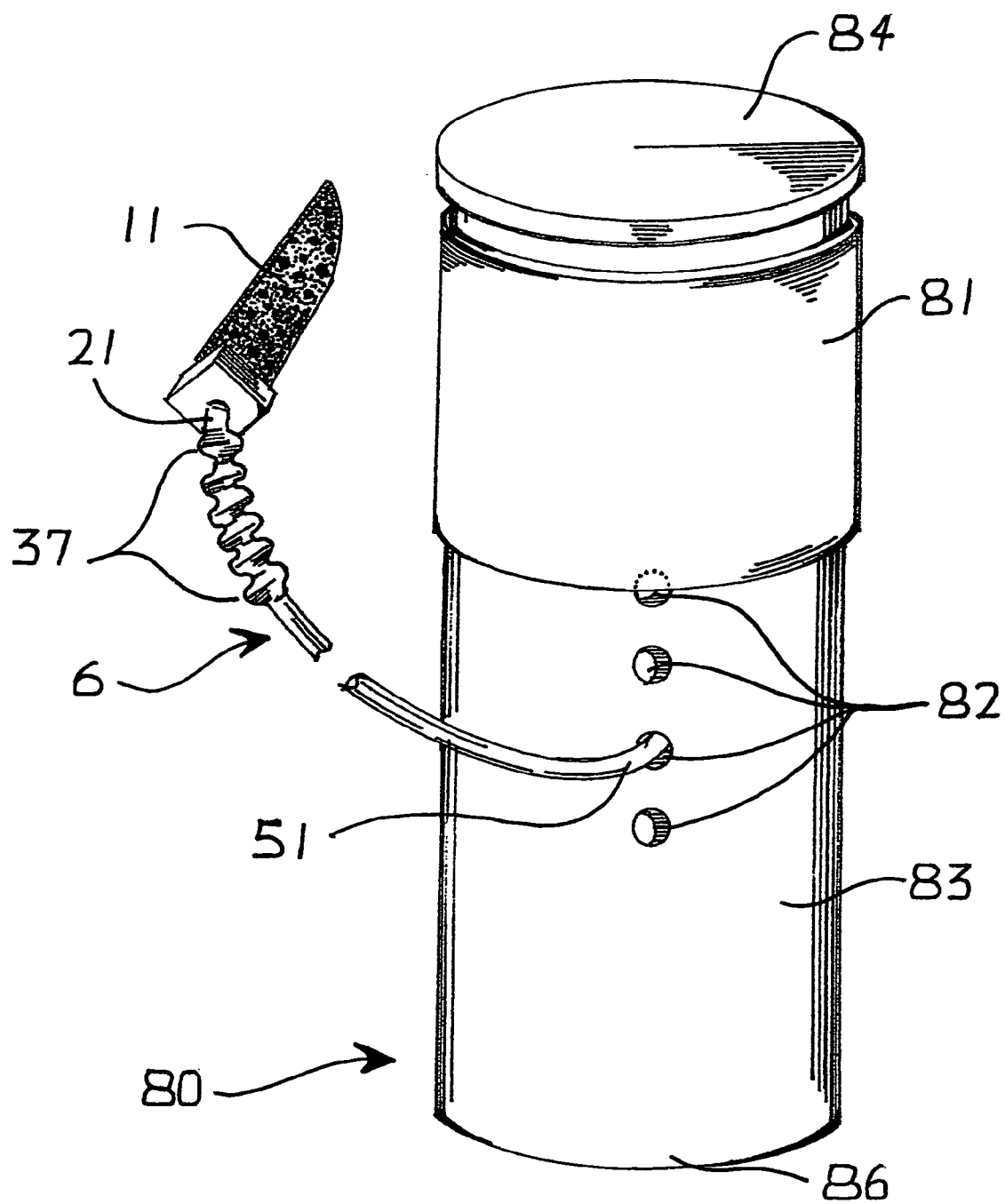
FIG. 8 shows alternate embodiment connecting to a specialized adapter device.

Alternate embodiment 6 shown in FIG. 8 illustrates a body 11 comprising of a porous material that will allow moisture to pass through it. Alternate embodiment 6 comprises a bendable portion having a plurality of peaks and valleys 37 at the distal end of tubing 21. The bendable portion may take a variety of forms as long as it results in a bendable portion. The proximal end of tubing 51 is shown maintaining the original diameter of distal end of tubing 21 and connecting directly to a specialized adapter device 80. The adapter device 80 is comprised of a hollow shaft having a closed top cap end 84 and a lower open end 86 suitable for connecting to a dental vacuum device, not shown. A tubular sleeve 81 is axially slideable on a shaft 83 to allow exposure of multiple apertures 82. The apertures 82 can accommodate multiple embodiments simultaneously. The top cap end 84 has a larger diameter to prevent the tubular sleeve 81 from sliding off the shaft 83. The shaft 83 and sleeve 81 are preferably comprised of any type of metal material but other materials may also be suitable.

I claim:

1. A dental apparatus comprising:
    a hollow and rigid dental wedge configured for insertion into an interproximal space between two teeth, comprising:
        a tapered body with at least one wall comprised of a plurality of apertures,
        a distal insertion end, and
        a proximal end; and
    a tube portion comprising:
        a distal end coupled to the proximal end of the dental wedge,
        a flexible portion, and
        a proximal end configured to connect to a vacuum device;
    wherein the dental wedge, once inserted, remains in place within the interproximal space and simultaneously aspirates fluid from and around the interproximal space upon activation of the vacuum device.

2. The dental apparatus of claim 1, wherein the distal end of the tube portion forms a rigid connection with the dental wedge, such that the distal end of the tube portion is employable as a gripping point of the apparatus.

3. The dental apparatus of claim 1, wherein the dental wedge is composed of plastic.

4. A dental apparatus comprising:
    a dental wedge configured for insertion into an interproximal space between two teeth, comprising:
        a tapered body composed of a porous material,
        a distal insertion end, and
        a proximal end; and
    a tube portion comprising:
        a distal end coupled to the proximal end of the dental wedge,
        a flexible portion, and
        a proximal end configured to connect to a vacuum device;
    wherein the dental wedge, once inserted, remains in place within the interproximal space and simultaneously aspirates fluid from and around the interproximal space upon activation of the vacuum device.

5. The dental apparatus of claim 4, wherein the distal end of the tube portion forms a rigid connection with the dental wedge, such that the distal end of the tube portion is employable as a gripping point of the dental apparatus.

6. The dental apparatus of claim 4, wherein the dental wedge is composed of plastic.

* * * * *